United States Patent [19] [11] 4,112,948
Kurtz et al. [45] Sep. 12, 1978

[54] SURGICAL DRAINAGE SYSTEM WITH PRESSURE INDICATOR AND ENCLOSED SOURCE OF LIQUID

[75] Inventors: Leonard D. Kurtz, Woodmere; Robert E. Bidwell, Melville, both of N.Y.

[73] Assignee: Deknatel, Inc., Queens Village, N.Y.

[21] Appl. No.: 684,315

[22] Filed: May 7, 1976

[51] Int. Cl.² ............................................. A61M 1/00
[52] U.S. Cl. ........................................ 128/276; 73/747
[58] Field of Search ................... 128/276, 295, 350 V, 128/272, 297, 275; 73/401, 747

[56] References Cited

U.S. PATENT DOCUMENTS

| | | | |
|---|---|---|---|
| 3,363,626 | 1/1968 | Bidwell et al. | 128/276 |
| 3,363,627 | 1/1968 | Bidwell et al. | 128/276 |
| 3,463,159 | 8/1969 | Heimlich | 128/350 V |
| 3,672,372 | 6/1972 | Heimlich | 128/295 X |
| 3,946,735 | 3/1976 | DeWall | 128/350 V X |

*Primary Examiner*—Robert W. Michell
*Assistant Examiner*—Michael H. Thaler
*Attorney, Agent, or Firm*—Larson, Taylor and Hinds

[57] ABSTRACT

A surgical drainage system is provided for the drainage of fluid from a body cavity which comprises a collection chamber, a U-tube manometer having one arm in fluid communication with the inlet to the collection chamber and a closed chamber in fluid communication with the other arm of the U-tube manometer. There is provided a rupturable container of liquid within one arm of the U-tube manometer such that when pressure is applied to the container a weakened seal breaks, thus allowing the liquid within the container to flow into the lower connected arms of the U-tube manometer. The U-tube manometer provides a visual indication of changes of pressure in the body cavity by oscillation of the liquid in the manometer. There is further provided a one way valve between the collection chamber and the inlet to the collection chamber. The one way valve permits fluids to flow from the body cavity into the collection chamber but prevents backflow of any higher pressure gas that might exist in the collection chamber.

7 Claims, 3 Drawing Figures

SURGICAL DRAINAGE SYSTEM WITH PRESSURE INDICATOR AND ENCLOSED SOURCE OF LIQUID

BACKGROUND OF THE INVENTION

1. Field of the Invention

This invention relates to surgical drainage systems and more particularly to apparatus for drainage fluids from a body cavity.

2. Description of the Prior Art

In order for a person to maintain a normal breathing pattern, his pleural cavity must be relatively free of fluids. These fluids, which may be generated in the cavity following, for example, lung surgery or pleurisy, obstruct normal pressure changes in the cavity, thereby interfering with breathing.

Many techniques have been employed to remove this fluid. One method for removing excess fluids is by means of "underwater drainage" systems such as shown in Bidwell et al. U.S. Pat. Nos. 3,363,626 and 3,363,627 and in Kurtz et al. U.S. patent applications, Ser. Nos. 621,600, now U.S. Pat. No. 4,015,603 and 621,601, now abandoned.

An examination of prior art systems reveals that there is a need for a drainage system which under emergency conditions must be immediately operable. It is desirable to provide a system having a valve serving as a seal to maintain reduced pressure conditions within the pleural cavity. Little time can be spared to fill manometer and liquid seals with fluids. Further, there is a need for a simple, inexpensive system made of transparent material with means for monitoring pleural cavity pressure conditions.

SUMMARY OF THE INVENTION

The present invention provides for a surgical drainage system that overcomes the disadvantages associated with the prior art devices noted hereinbefore. There is provided a pressure fluctuation indication means that can instantaneously indicate the rate of pressure fluctuation within the pleural cavity. This system is simple and may be made operable, especially in emergency situations, with only minimal preparation. Further, this invention combines therewith a rupturable enclosed fluid source for the rapid filling of a manometer. Finally this invention is of simple construction, inexpensive an easily placed in an antiseptic state.

In accordance with a preferred embodiment of the invention, a surgical drainage system is provided which comprises a first collection compartment in fluid communication with a cavity to be drained and a second closed compartment. A manometer is used in series to place the first collection compartment in fluid communication with the second compartment. Finally, a closed rupturable container containing liquid is positioned in one arm of the manometer.

Additional features an advantages of the invention will be set forth in, or be apparent from, the detailed description of the preferred embodiments of the invention found hereinbelow.

DETAILED DESCRIPTION OF THE PREFERRED EMBODIMENTS

Figure 1:
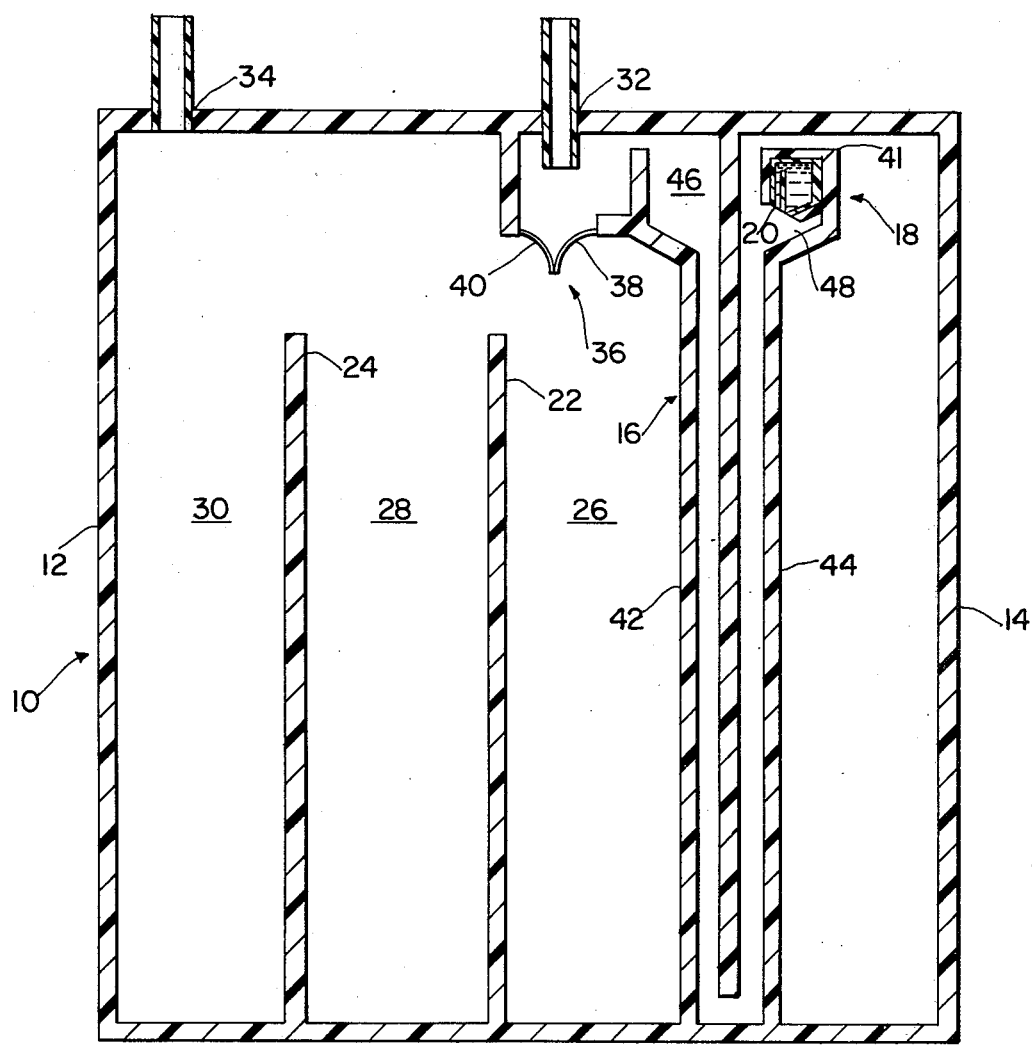
FIG. 1 is a cross-sectional elevation view of the apparatus in accordance with the invention.
Figure 3:
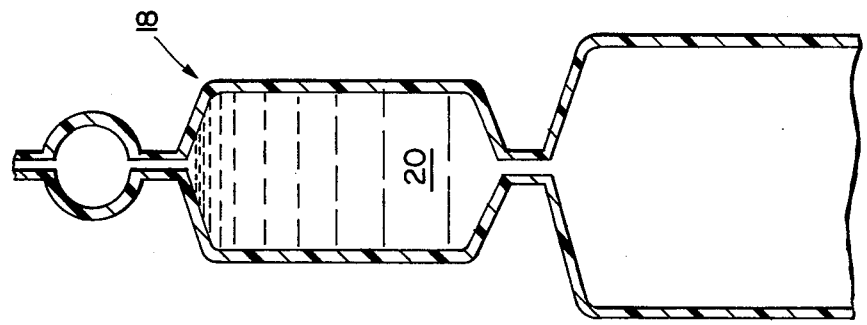
FIG. 3 is a cross-sectional view taken along line 3—3 in FIG. 2.
Figure 2:
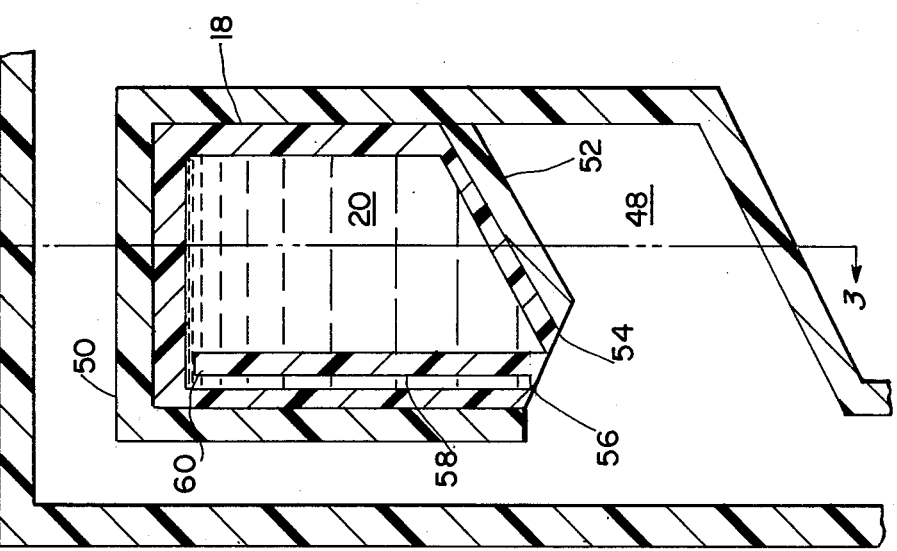
FIG. 2 is an enlarged portion of the invention as depicted in FIG. 1.

With reference to the figures and, in particular, to FIG. 1, there is disclosed a preferred embodiment of surgical drainage system 10. For purposes of description, system 10 can be divided into the following functional units: a first collection compartment 12 capable of being placed in fluid communication with a cavity to be drained, a second compartment 14, a manometer 16 that places first collection compartment 12 in fluid communication with second compartment 14, and a closed chamber 18 containing liquid 20 located in manometer 16.

The collection chamber 12 is designed for receiving the fluid drained from a body cavity. As shown in FIG. 1, the middle and lower portions of rectangularly shaped compartment 12 are partitioned by baffles 22 and 24 into three smaller chambers 26, 28 and 30. Drained fluid fills the smaller chambers sequentially starting with chamber 26, excess fluid then overflowing into chamber 28 and so on until all three chambers are filled. It should be noted since compartment 12, as well as the entire system 10, is comprised of a transparent material, the amount of fluid in collection chamber 12 can be quickly determined by observing the filled state of these smaller chambers 26, 28 and 30. Further, scales may be applied to the external surface of these chambers 26, 28 and 30 to facilitate the determination of the fluid content of collection chamber 12. Finally the number and size of these smaller chambers may be changed so as to accommodate various rates and amounts of drained fluid and so as to better indicate these amounts and rates to an observer.

An inlet aperture 32 and an outlet aperture 34 are also provided in the upper surface of collection compartment 12. Through inlet aperture 32, collection chamber 12 is placed in fluid communication with a cavity to be drained (not shown). Through outlet aperture 34, chamber 12 is placed in communication with a source of vacuum (not shown). This vacuum source is used to maintain the desired negative pressure in compartment 12 and the draining cavity.

Finally compartment 12 is provided with a one way valve 36 to provide a seal to prevent higher pressure from the collection chamber from passing into the pleural cavity. This one way valve is located directly below inlet aperture 32 an directly above chamber 26. One way valve 36 includes two flexible flaps 38 and 40 that are downwardly dependent from the upper surface of compartment 12. Flexible flaps 38 and 40 describe downwardly concave arcs that touch each other at their lowermost point. Fluid can readily flow from aperture 32, separate flaps 38 and 40 and continue into chamber 26. However, flaps 38 and 40 press against each other and prevent the cavity from being exposed to atmospheric pressure should the vacuum source be inadvertently disconnected from aperture 34. Further flaps 38 and 40 prevent fluid from splashing or flowing back toward aperture 32 or into manometer 16.

Compartment 12, as well as compartment 14 and manometer 16, can be constructed of any tough, rigid, impact-resistant, transparent plastic capable of being antiseptically cleaned. Further, system 10 can be of one-piece construction using a method of manufacture such as, for example, blow molding, pressure forming, injection molding or slush molding. In the alternative, however, the elements may be individually manufactured and connected into an integral unit.

Compartment 14 is located adjacent to chamber 26 of collection compartment 12. Compartment 14 has only one aperture 41 and it is through aperture 41 that compartment 14 is placed in fluid communication with manometer 16.

Manometer 16 is disposed between collection chamber 12 and compartment 14. Manometer 16 includes first and second tubes 42 and 44 respectively. Tubes 42 and 44 are placed in fluid communication at their lower ends so as to form a generally U-shaped manometer. The uppermost end of first tube 42 is in fluid communication with the upper portion of collection compartment 12 between inlet aperture 32 and one way valve 36. Also, the uppermost end of second tube 44 is in fluid communication with the upper portion of compartment 14. Thus, compartment 14 is placed in fluid communication with collection chamber 12 through manometer 16. Further, the volume of manometer 16 is small in comparison to the volume of compartment 14.

At the uppermost ends of first and second tubes 42 and 44 are first and second overflow chambers 46 and 48. Essentially chambers 46 and 48 are enlargements of first and second tubes 42 and 44 respectively. As will be described later in more detail, when fluid is introduced into manometer 16, chambers 46 and 48 prevent this fluid from overflowing into collection chamber 12 or compartment 14.

Disposed above the enlarged volume forming overflow chamber 48 there is provided a rupturable container 18 which contains a liquid 20.

Container 18 is held in the position shown by a mounting enclosure 50. Mounting enclosure 50 includes an inclined lower surface 52 located directly above overflow chamber 48. Further, an aperture 54 is formed at the lowermost point of inclined surface 52. Mounting enclosure 50 is comprised of a clear plastic that will flex when moderate pressure, such as that exertable by a human hand, is placed thereon.

Container 18 comprises a deformable, heat sealable material and further includes a weakened seal 56 and vent 58. Weakened seal 56 is positioned opposite aperture 54 in lower surface 52 of mounting enclosure 50. Vent 58 comprises a tube 60. The volume of tube 60 is small in comparison to the volume of closed container 18. The lower end of tube 60 is in fluid communication with the upper portion of container 18. Tube 60 as well as the sides of container 18 except for weakened seal 56 is defined by wide heat sealed strips. Weakened seal 56 is also defined by a heat sealed strip; however, this strip is narrow in comparison to the strips defining container 18.

Pressure placed on container 18 forces fluid against and ruptures weakened seal 56. As fluid drains from container 18 into manometer 16, gas flows through vent 58 and replaces the draining fluid. In manometer 16, the liquid creates a seal between collection chamber 12 and compartment 14.

As previously mentioned, system 10 comprises a moldable plastic material. As a one piece structure, system 10 can be constructed of two half shells. In the preferred embodiment, container 18 with liquid 20 is placed in a portion of mount enclosure 50 in one of the half shells before the shells are bonded together. Thus, container 18 is enclosed in mounting enclosure 50.

The operation of surgical drainage system 10 is as follows. First, compartment 12, through aperture 34, is placed in fluid communication with a source of vacuum. Subsequently, collection chamber 12, through aperture 32, is place in fluid communication with the cavity to be drained. Pressure, as created by human hands, placed on mounting enclosure 50 is transmitted through the walls of enclosure 50 to container 18. This pressure forces fluid against and ruptures weakened seal 56. Fluid flows from container 18 partially filling first and second tubes 42 and 44 of manometer 16 and creates a liquid seal between collection chamber 12 and compartment 14. The vacuum will maintain a desired level of negative pressure in collection chamber 12 and the draining cavity. Thus the normal breathing pattern is not interrupted.

Since the volume of manometer 16 is insignificant in comparison to compartment 14, the flow of fluid in manometer 16 between first and second tubes 42 and 44 does not change the pressure in compartment 14. Thus, any oscillations of fluid in manometer 16 are not affected by back pressure in compartment 14. Since changes in pressure in the pleural cavity cause the fluid in manometer 16 to oscillate and since back pressure in compartment 14 does not influence these oscillations, these pressures changes can be easily and quickly monitored by visually observing these oscillations within manometer 16. Further, overflow chambers 46 and 48, by collecting excess fluid, prevent the fluid in manometer 16 from spilling into compartments 12 or 14.

As fluid drained by the pleural cavity fills chamber 26, the amount of fluid can be visually observed and scales can be placed on the front elevational wall of system 10 to provide an accurate determination of the amount of fluid being drained from the patient.

When chamber 26 becomes filled, it overflows into chamber 28 and chamber 28, when filled, in turn overflows into chamber 30. Once chambers 26, 28 and 30 have been filled, the remaining upper portions of first compartment 12 is used to contain further amounts of drained fluid.

Although the present invention has been described relative to an exemplary embodiment thereof, it will be understood by those skilled in the art that variations and modifications can be effected in these embodiments without departing from the scope and spirit of the invention.

I claim:

1. A surgical drainage system for the drainage of a cavity comprising,
   a collection chamber adapted to be in fluid communication with the cavity to be drained,
   a compartment disposed adjacent said collection chamber, said compartment having a single opening therein,
   a U-tube manometer placing said collection chamber in fluid communication with said compartment through said single opening in said compartment,
   said U-tube manometer having first and second tubes in fluid communication at their lower ends so as to form a U shape, said collection chamber being in fluid communication with the upper end of said first tube, said compartment being in fluid communication with the upper end of said second tube of said U-tube manometer, the volume of said manometer being small with respect to the volume of said compartment and, means for storing a liquid in fluid communication with said manometer, said storing means comprising a rupturable container located at the upper end of said second tube.

2. A surgical drainage system in accordance with claim 1 wherein said container is held in said manometer by a mounting enclosure and wherein said container has a weakened seal such that force placed on said container breaks said seal allowing the liquid to flow into said manometer whereby said compartment is sealed from said collection chamber by the fluid in said manometer, said manometer for providing a visual indication of any oscillation of fluid therein caused by changes in cavity pressure.

3. A surgical drainage system in accordance with claim 2 wherein said mounting enclosure includes a lowermost surface, said surface being an aperture therethrough.

4. A surgical drainage system in accordance with claim 2 wherein said container has a vent, said vent comprising a tube, the volume of said tube being small in comparison to the volume of said container, the lower end of said tube closed by a portion of said weakened seal, the upper end of said tube being in fluid communication with the upper en of said closed compartment, said tube allowing gases to replace the liquid that flows from the container when the said weakened seal is broken.

5. A surgical drainage system in accordance with claim 2 wherein the upper ends of said first and second tubes of said manometer are enlarged to form first and second overflow chambers to collect the fluid and prevent the fluid in said manometer from overflowing into said collection chamber and into said second chamber.

6. A surgical drainage system in accordance with claim 1 wherein said collection chamber is partitioned into a plurality of sections and wherein said collection chamber has a aperture means for placing a vacuum source in communication with said collection chamber.

7. A surgical drainage system in accordance with claim 1 wherein said collection chamber includes a one way valve means for placing the collection chamber in fluid communication with the cavity to be drained, said valve means including flaps downwardly dependent from said upper surface of said collection chamber and for preventing the cavity from becoming exposed to atmospheric pressures.

* * * * *